United States Patent [19]

Sklebitz et al.

[11] Patent Number: 4,458,359
[45] Date of Patent: Jul. 3, 1984

[54] X-RAY DIAGNOSTIC INSTALLATION FOR X-RAY TOMOGRAPHIC IMAGES

[75] Inventors: Hartmut Sklebitz, Erlangen; Wolfgang Maass, Nuremberg, both of Fed. Rep. of Germany

[73] Assignee: Siemens Aktiengesellschaft, Berlin & Munich, Fed. Rep. of Germany

[21] Appl. No.: 469,980

[22] Filed: Feb. 25, 1983

[30] Foreign Application Priority Data

Mar. 4, 1982 [DE] Fed. Rep. of Germany ....... 3207816

[51] Int. Cl.$^3$ .......................... A61B 6/00; H01J 31/50; H05G 1/64
[52] U.S. Cl. ......................................... 378/22; 378/99
[58] Field of Search ...................... 378/21, 22, 25, 26, 378/23, 24, 27, 99

[56] References Cited

U.S. PATENT DOCUMENTS 4,149,082  4/1979  Haendle et al. ................. 250/445 T

FOREIGN PATENT DOCUMENTS 3113368 of 1982 Fed. Rep. of Germany .

Primary Examiner—Alfred E. Smith
Assistant Examiner—T. N. Grigsby
Attorney, Agent, or Firm—Hill, Van Santen, Steadman & Simpson

[57] ABSTRACT

An exemplary embodiment comprises at least one X-ray source for the generation of an X-ray beam, a control generator for effecting movement of the X-ray beam, a patient support, an X-ray image intensifier which is surrounded by deflection coils which are connected with a deflection circuit (connected to the control generator) for effecting the synchronous movement of the electron image in the X-ray image intensifier, and a television chain coupled to the output of the X-ray image intensifier, in which the deflection coils consist of n coil pairs offset relative to one another in one plane, whereby n amounts to at least three. The deflection device is so designed that the deflection current flows only in respectively two of the n coil pairs.

2 Claims, 2 Drawing Figures

X-RAY DIAGNOSTIC INSTALLATION FOR X-RAY TOMOGRAPHIC IMAGES

BACKGROUND OF THE INVENTION

The invention relates to an X-ray diagnostic installation for X-ray tomographic images, comprising at least one X-ray source for generating an X-ray beam, comprising a control generator for effecting movement of the X-ray beam for the purpose of irradiating the patient from various directions, comprising a patient support, comprising an X-ray image intensifier which is surrounded by deflection coils which are connected wih a deflection device (connected to the control generator) for effecting the synchronous movement of the electron image in the X-ray image intensifier, and comprising a television chain coupled to the output of the X-ray intensifier. With this X-ray diagnostic installation one obtains X-ray tomographic images of body layers extending in a longitudinal direction of the patient.

In the German OS No. 27 12 320 (U.S. Pat. No. 4,149,082 issued Apr. 10, 1979) such an X-ray diagnostic installation is described in which, by means of a synchronous movement of the X-radiation and of the image field of the X-ray image intensifier, a body layer can be sharply imaged whereas all other body parts not lying in this layer are suppressed through lack of sharp definition. The desired layer can be selected through the alteration of the deflection of the electron image in the X-ray image intensifier. Two coil pairs, arranged about the X-ray image intensifier, generate a magnetic field which effects the deflection of the electron image of the X-ray image intensifier.

The two coil pairs are arranged about the X-ray image intensifier; the coils are energized corresponding to the range of deflection of the electron image in the X-ray image intensifier; the level of energization of the coils is dependent upon the required maximum layer height (or level); and the coils must, under certain circumstances, be subjected to high currents so that distortions of the magnetic field may occur which impair the resolution of the tomographic image. These distortions restrict the possible layer height range. In addition, high demands are here made of the X-ray image intensifier. Even small differential distortions which, in particular, occur in the direction of the border of the X-ray image intensifier, restrict the usable range of the input image of the X-ray image intensifier, as a consequence of which the maximally possible layer height is further reduced. Furthermore, during the utilization of, for example, rectangular waveform currents for the deflection coils, comet tail-shaped image distortions occur which likewise impair the resolution of the X-ray tomographic image.

SUMMARY OF THE INVENTION

The invention proceeds from the objective of producing an X-ray diagnostic installation of the type initially cited which renders possible a constant (or uniform) deflection with reduced current amplitude, so that deformations are prevented and distortions are compensated.

In accordance with the invention, the objective is achieved in that the deflection coils consist of n coil pairs, a respective coil of each pair being offset relative to a respective more remote coil of other pairs by 360°/n in one plane, where n amounts at least to three, and in that the deflection device is so designed that the deflection current flows only in respectively two of the n coil pairs. Through this arrangement it is achieved that, for the generation of a magnetic field, the current flowing through the coils is always distributed over two pairs of coils so that a lower current flows through the individual coils than is necessary for the deflection.

The differential distortions of the X-ray image intensifier can be particularly well compensated if the deflection device generates voltages which exhibit a staircase waveform progression, whereby each staircase step is associated with an X-ray source, if the deflection device is provided with a generator circuit which, for the transitions from step to step, generates, for each step of the step function, an e-function which is separately adjustable through adjustment means, and if the deflection device is provided with a superimposition stage in which the staircase voltage and the e-function are superimposed, and if the staircase voltage progression approximates itself, from an initial value which corresponds to the voltage value of the preceding staircase step level, to an end value in the form of the e-function which corresponds to the desired staircase step increment. A simple construction of the deflection device is achieved through the measures disclosed in the additional claims of the present case.

The invention shall be explained in greater detail in the following on the basis of an exemplary embodiment illustrated on the accompanying drawing sheet; and other objects, features and advantages will be apparent from this detailed disclosure and from the appended claims.

DETAILED DESCRIPTION

Figure 1:
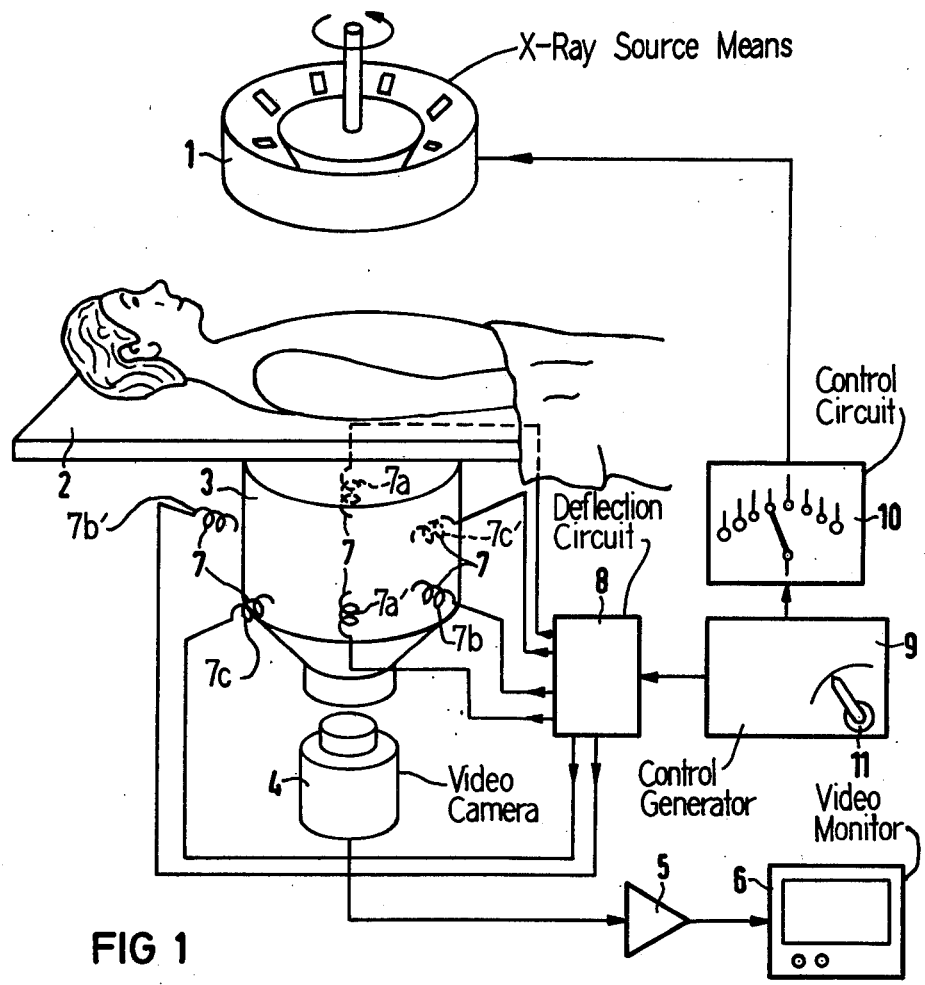
FIG. 1 illustrates an X-ray diagnostic installation according to the invention.

In FIG. 1, an X-ray diagnostic installation comprising an X-ray tube 1 is illustrated which exhibits a circular ring-shaped arrangement of grid controlled cathodes which are arranged about a rotary anode. An X-ray tube of this type is described in the German patent application P 31 13 368.1. The high voltage transformer for the X-ray tube 1 is not illustrated. The X-ray tube 1 generates X-ray beams which penetrate a patient lying on a patient support 2 and project radiation images onto the inlet fluoroscent screen of an X-ray image intensifier 3. The output signal of the X-ray image intensifier 3 is picked up by a television camera 4 whose output signal is amplified in a video amplifier 5 and reproduced on a monitor 6.

The deflection of the electron image in the X-ray image intensifier 3, which is necessary for the tomographic technique, is magnetically achieved by means of three pairs of deflection coils 7. The activation of the deflection coils 7 proceeds through a deflection device 8 which is synchronized by a control generator 9. The control generator 9 effects, synchronously with the image displacement in the X-ray image intensifier 3, via a control device 10, the step-by step switching on of the grids of the X-ray tube 1. An adjustment means, which can be designed in the form of a potentiometer, is manually controllable by means of an actuator 11 which may be mounted on the control generator 9 and determines the maximum deflection amplitude and thereby the height of the observed body layer.

Instead of the X-ray tube 1, also several individual X-ray tubes can be provided which can be arranged circularly, linearly, or randomly distributed, and which are switched on synchronously with the deflection of the X-ray image intensifier 3. However, an X-ray focal spot can also be employed which is mechanically moved.

The body layer, whose details are represented on the monitor 6 in a sharply defined fashion, in addition to being capable of being selected through intensity alteration of the magnetic image deflection, can also be selected through adjustment of the special interval between the X-ray tube 1 and the patient support 2 as well as between the patient support 2 and the X-ray image intensifier 3.

Figure 2:
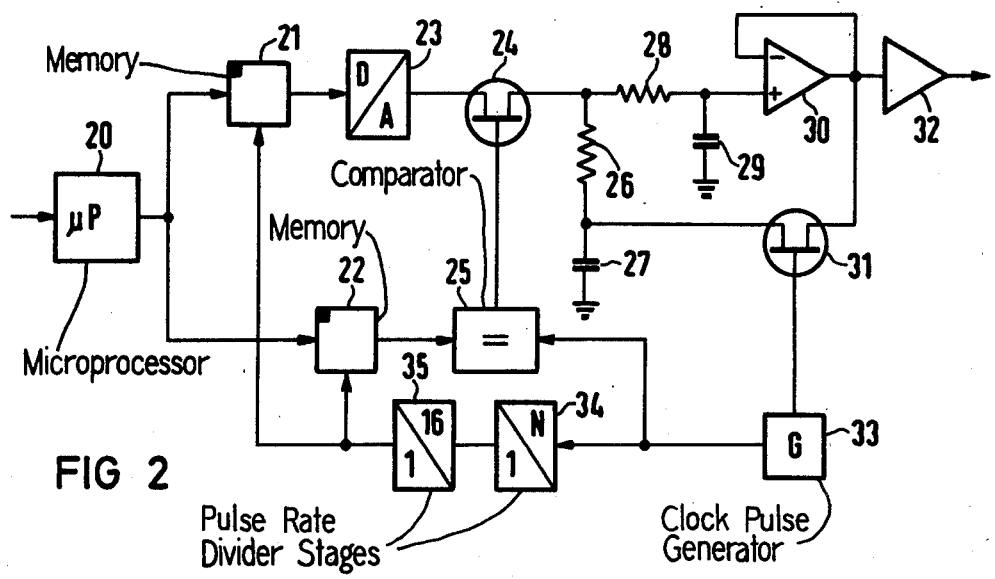
FIG. 2 is a detailed block circuit diagram illustrating a deflection system for association with one of the deflection coils of FIG. 1.

In FIG. 2, a microprocessor 20 is illustrated whose data output is connected with the inputs of two random access memories (RAM) 21 and 22. The output of the memory 21 is connected to a digital-to-analog converter 23 which is connected with the source terminal of a field effect transistor (FET) 24. The one input of a comparator 25 is connected with the memory 22, and the output of the comparator is connected to the gate terminal of the FET 24. Connected with the drain terminal of the field effect transistor 24 are two resistances 26 and 28 whose other terminals are connected to ground via capacitors 27 and 29. The connection point of the capacitor 29 and of the resistance 28 is connected to the non-inverting input of an operational amplifier 30. The output of the operational amplifier 30 is connected with its inverting input. A field effect transistor 31 connects the output of the operational amplifier 30 and the connection point between the resistance 26 and the capacitor 27. The output voltage of the operational amplifier 30, which is connected as an impedance converter, is linearly converted into current values by means of an output amplifier 32, which current values are supplied to a deflection coil 7. For each of the deflection coils 7 an activation circuit 21 through 32 must be provided. However, they are not all illustrated in FIG. 2 in order that the illustration will not become unclear. A generator 33 generates the switching pulses for the FET 31 and clock pulses which are supplied to the comparator 25 and to a first divider 34. This first divider 34 divides the clock pulses corresponding to the number of coil pairs. The output signal of the first divider 34 is divided in a second divider 35, for example, by sixteen. The output of this divider 35 is connected with the clock pulse inputs of the memories 21 and 22.

From the adjustment means 11 of the control generator 9 a signal is supplied to the microprocessor 20 which corresponds to a selected layer height. The deflection data required for this specific layer height are transmitted from the microprocessor into the memory 21. In synchronism with the clock pulse rate for effecting the switching-on of the X-ray sources these deflection data are read out. At the output of the D/A converter 23, analog deflection amplitudes for the control of the deflection currents are available which form a staircase shaped progression. For the determination of the time constants of the e-function, data are simultaneously transmitted into the memory 22 which likewise are read out at the clock pulse rate of switching on of the X-ray sources. The comparator 25, through comparison of the clock pulses with the respective data, delivers switching pulses of predetermined length, so that the voltage connected to the output of the D/A-converter 23 is through-connected through the FET 24. The length of the switching pulses determines the charging rate of the capacitor 27. Since the comparison frequency in this example with three coil pairs (n=3) lies forty-eight (16 times n) times higher than the switching frequency of the x-ray sources, one obtains at the condenser 27 virtually an e-function. The resistance 28 and the capacitor 29 represent a low pass filter which suppresses the residues of the high switching frequency of the FET 24. The time constant of the low pass filter 28, 29, is considerably smaller than that of the resistance 26 and of the capacitor 27. At the output of the amplifiers 30 and 32 there is thus connected a voltage with a progression of an e-function. After completed radiographic exposure the respective X-ray source is blocked and prior to the switching over to the next staircase step, the FET 31 receives from the generator 33 a brief switching pulse, so that the voltage value of the now-terminated staircase step, corresponding to the final value of the current amplitude, is stored in the capacitor 27. Now a new address is applied to the memories 21 and 22 so that the next staircase step can be generated. Simultaneously the X-ray source corresponding to the staircase step is switched on. As already described, the capacitor 27 is further charged charged corresponding to the adjusted e-function.

Through such measures, additionally resolution reductions due to apparatus twisting during tilting of the apparatus, due to variable earth magnetism influences during tilting, and due to incomplete centering (or alignment) of radiator and X-ray image intensifier can be avoided.

For the various layer heights, the data for the deflection amplitudes are stored in a memory region of the microprocessor. If intermediate steps are required, the latter can be formed through interpolation in the microprocessor.

For the adjustment of the deflection currents, the stored data can be corrected by non-illustrated adjustment means. However, this can also take place through a switching-over of the addresses by the microprocessor.

The adjustment is advantageously conducted with the aid of a small steel sphere. Given approximately maximum layer height, the adjustment for each of the X-ray sources with respect to each deflection axis is varied for so long until the steel sphere is imaged free of comet tail-shaped image distortions.

It will be apparent that many modifications and variations may be made without departing from the scope of the teachings and concepts of the present invention.

SUPPLEMENTAL DISCUSSION

For the case of three pairs of deflection coils 7 as illustrated in FIG. 1, the n coil pairs (n equals three) are offset relative to one another by 360°/n in the sense that one coil of each axially opposing pair is offset from a corresponding coil of the other pair or pairs by 120° for n equals three. If the coil pairs are designated A, B and C and a coil 7a is considered to be located at twelve o'clock, then the other coil of this pair A is designated 7a' and is located at six o'clock. If coil 7b of pair B is located at four o'clock, then coil 7b' is located at ten o'clock. Further, if coil 7c of pair C is located at eight o'clock, then the other coil of this pair is located at two o'clock. It will be observed that coils 7a, 7b and 7c are separated by 360°/3 or 120°; and also coils 7a', 7b' and 7c' are separated by 360°/3 or 120°.

For the case of four coil pairs A, B, C and D, a first coil of pair A might be at twelve o'clock and the second coil of pair of A would be at six o'clock, while a first coil of pair B would be at three o'clock and a second coil of pair B would be at nine o'clock. Thus, for n equals four, the first coils of pairs A and B would be separated by 360°/4 or 90°, and the second coils of pairs A and B would be separated by 360°/n or 90°. If a first coil of pair C was at 1:30 o'clock, then the second coil of pair of C would be at 7:30 o'clock, and the first coil of pair D would be at 4:30 o'clock, and the second pair of coil D would be at 10:30 o'clock. Again, the corresponding coils of the pairs C and D would be separated by 360°/4 or 90°.

For the case of five coil pairs A, B, C, D and E, a first coil of pair A might be located at twelve o'clock, a first coil of pair B might be located at 2:24 o'clock, a first coil of pair C might be located at 4:48 o'clock, a first coil of pair D might be located at 7:12 o'clock, and a first coil of pair E might be located at 9:36 o'clock. As before, the second coils of each pair will be offset by 180° from the respective first coils, so that the second coils will also be offset by angles of 360°/5 or 72°.

In each of the foregoing cases, for a given resultant desired magnetic field in the plane of the coils 7 (e.g. at right angles to the vertical axis of the image intensifier 3), only two coil pairs would receive deflection current by means of a respective deflection circuit such as that illustrated in FIG. 2.

For example, with the six coils of the respective pairs numbered as shown in FIG. 1, the coil pairs 7b, 7b', and 7c, 7c' would both be active to produce deflection of the electron image along an axis coincident with the axis of coils 7a and 7a'. Later, for deflection of the electron image along an axis of 30° (at right angles to the axes of coils 7b, 7b'), the coils 7b, 7b' would be de-energized, and coils 7a, 7a' and 7c, 7c' would receive essentially maximum currents, neglecting secondary influences, e.g. compensation for the earth's magnetic field or the like.

We claim as our invention:

1. An X-ray diagnostic installation for producing X-ray tomographic images, comprising X-ray source means (1) for the generation of an X-ray beam, control generator means (9) for effecting the movement of the X-ray beam for the purpose of irradiating the patient from respective beam directions, a patient support (2), an X-ray image intensifier (3) having deflection coil means (7), deflection circuit means (8), connected to the control generator means (9) and with the deflection coil means for effecting movement of the electron image in the X-ray image intensifier (3) sychronously with the changing of the beam direction of the X-ray source means, and a television chain (4 through 6), coupled to the output of the X-ray image intensifier (3), characterized in that the deflection coil means (7) comprises n coil pairs offset relative to one another by 360°/n in one plane, where n amounts at least to three, and that the deflection circuit means (8) is so designed that the deflection current flows only in two of the n coil pairs, respectively.

2. An X-ray diagnostic installation according to claim 1, with said deflection circuit means comprising deflection current output circuit means connected with said deflection coil means, first and second memories having respective data inputs, microprocessor means connected with the data inputs of the memories, and being controlled to supply control values to the memories in accordance with a desired sequence of energizing currents to be supplied to said deflection current output circuit means for effecting corresponding positioning of the electron image of said X-ray image intensifier digital to analog converter means connected with the output of the first memory for supplying analog outputs in accordance with respective control values stored by the first memory, and further comprising first and second resistance-capacitance networks with different first and second time constants and including respective first and second capacitance means, switch means controlling the supply of analog outputs from the converter means to said second resistance-capacitance network to effect charging of said second capacitance means, voltage to current converter means coupled with said first capacitance means and with said second resistance-capacitance network for supplying a deflection current to the deflection current output circuit means in accordance with a summation of the voltages on said first and second capacitance means, timing means controlled by the control values stored by the second memory and controlling said switch means to supply charge to the second capacitance means during a time interval in accordance with one of said control values stored by said second memory, and means for incrementing the charge on said first capacitance means at the end of each time interval in accordance with the attained value of the deflection current output produced by said voltage to current converter means.

* * * * *